(12) United States Patent
Dai et al.

(10) Patent No.: US 12,173,375 B2
(45) Date of Patent: Dec. 24, 2024

(54) METHODS FOR THE RAPID AMPLIFICATION OF HEPATITIS B VIRUS NUCLEIC ACID

(71) Applicant: SANSURE BIOTECH INC., Hunan (CN)

(72) Inventors: Lizhong Dai, Changsha (CN); Xu Fan, Changsha (CN)

(73) Assignee: SANSURE BIOTECH INC., Hunan (CN)

( * ) Notice: Subject to any disclaimer, the term of this patent is extended or adjusted under 35 U.S.C. 154(b) by 440 days.

(21) Appl. No.: 17/258,152

(22) PCT Filed: Jan. 31, 2019

(86) PCT No.: PCT/CN2019/074284
§ 371 (c)(1),
(2) Date: Jan. 5, 2021

(87) PCT Pub. No.: WO2020/007042
PCT Pub. Date: Jan. 9, 2020

(65) Prior Publication Data
US 2021/0277490 A1    Sep. 9, 2021

(30) Foreign Application Priority Data

Jul. 5, 2018  (CN) .......................... 201810728131.X

(51) Int. Cl.
*C12Q 1/70* (2006.01)
(52) U.S. Cl.
CPC .................................. *C12Q 1/706* (2013.01)
(58) Field of Classification Search
CPC .. C12Q 1/706; C12Q 1/686; C12Q 2563/107; C12Q 2527/113
See application file for complete search history.

(56) References Cited

U.S. PATENT DOCUMENTS

| 2010/0203594 A1 | 8/2010 | Segawa et al. |
| 2010/0279392 A1 | 11/2010 | Kodama et al. |
| 2014/0073013 A1 | 3/2014 | Gorman et al. |

FOREIGN PATENT DOCUMENTS

| CN | 201534842 | 7/2010 |
| CN | 101802163 | 8/2010 |
| CN | 102174660 | 9/2011 |
| CN | 102174660 A * | 9/2011 |
| CN | 204848844 | 12/2015 |
| CN | 106399053 | 2/2017 |
| CN | 107312874 | 11/2017 |
| CN | 108913811 | 11/2018 |
| DE | 10222275 | 12/2003 |
| EP | 2322647 | 5/2011 |

OTHER PUBLICATIONS

Shoffner et al. Nucleic Acids Research, 1996, vol. 24, No. 2, 375-379. (Year: 1996).*
Hataoka et al. Analytical Science 2005, 21:53-56. (Year: 2005).*
Northrup et al. A miniature analytical instrument for nucleic acids based on micromachined silicon reaction chambers. Anal Chem. Mar. 1, 1998;70(5):918-22. (Year: 1998).*
Huang G et al. A rapid, low-cost, and microfluidic chip-based system for parallel identification of multiple pathogens related to clinical pneumonia. Sci Rep. Jul. 25, 2017;7(1):6441. (Year: 2017).*
"Search Report of Europe Counterpart Application", issued on Mar. 24, 2022, p. 1-p. 9.
"International Search Report (Form PCT/ISA/210)" of PCT/CN2019/074284, mailed on Apr. 30, 2019, with English translation thereof, pp. 1-9.
"Written Opinion of the International Searching Authority (Form PCT/ISA/237)" of PCT/CN2019/074284, mailed on Apr. 30, 2019, with English translation thereof, pp. 1-9.
"Office Action of China Counterpart Application", issued on Dec. 27, 2019, with brief English translation thereof, p. 1-p. 15.
"Office Action of China Counterpart Application", issued on Mar. 31, 2020, with brief English translation thereof, p. 1-p. 4.
Zhou Tian, et al., "Design, fabrication of micro—chamber PCR chip and realization of sample amplification." Journal of Functional Materials and Devices, vol. 9, No. 2, Jun. 2003, pp. 191-194.
Wang Jin-Feng, et al., "Simultaneous rapid detection of 9 kinds of foodborne bacteria by GNM C7-8 real-time PCR." Journal of Food Safety and Quality, vol. 9, No. 9, May 2018, pp. 2090-2095.
Wu Xioayun, et al., "SpeedCycler2 with Rapid PCR Technology." Modern Scientific Instruments. No. 4, Aug. 2011, pp. 131-134.

* cited by examiner

*Primary Examiner* — Nicole Kinsey White
*Assistant Examiner* — Ruixue Wang
(74) *Attorney, Agent, or Firm* — JCIP GLOBAL INC.

(57) ABSTRACT

A rapid amplification method for a nucleic acid of hepatitis B virus, comprises the following steps: mixing a sample containing hepatitis B virus with a nucleic acid releasing agent, and adding a PCR premix to obtain a reaction solution, the PCR premix comprising deoxyribonucleoside triphosphate, an upstream primer as shown in the sequence SEQ ID NO: 1, a downstream primer as shown in the sequence SEQ ID NO: 2, a DNA polymerase and an amplification buffer; placing the reaction solution in a PCR reaction tube so that the reaction solution is in a form of a thin film with a thickness of 0.1 mm or less; performing PCR amplification under the following reaction condition: pre-denaturation at 90 to 100° C. for 10 s to 600 s, denaturation at 90 to 100° C. for 0 to 1 s, and annealing and extending at 50-65° C. for 0 to 1 s.

7 Claims, 5 Drawing Sheets
Specification includes a Sequence Listing.

METHODS FOR THE RAPID AMPLIFICATION OF HEPATITIS B VIRUS NUCLEIC ACID

CROSS-REFERENCE TO RELATED APPLICATION

This application is a 371 application of International PCT application serial no. PCT/CN2019/074284, filed on Jan. 31, 2019, which claims the priority benefit of China application no. 201810728131.X, filed on Jul. 5, 2018. The entirety of each of the above-mentioned patent applications is hereby incorporated by reference herein and made a part of this specification.

BACKGROUND

Technical Field

The disclosure relates to the field of biochemistry, in particular to a method for rapid amplification of hepatitis B virus nucleic acid.

Description of Related Art

Hepatitis B virus (HBV) is a kind of DNA virus, belonging to the family Hepadnaviridae. There are approximately 257 million people infected with HBV around the world, and 93 million in China. Thus, research on the hepatitis B virus has received attention worldwide. In the scientific research related to hepatitis B virus, it is often required to perform amplification of hepatitis B virus nucleic acid for non-disease diagnosis or treatment purposes to obtain a large amount of hepatitis B virus nucleic acid, in order to provide samples for various scientific experiments.

Polymerase chain reaction (PCR) is a major in vitro nucleic acid amplification technology, which has been developing rapidly in recent years. The characteristic of PCR technology is to simulate the process of DNA replication in organisms. Under suitable temperature conditions, using templates, primers, the polymerase and other materials needed for amplification, the target DNA or RNA fragments undergo continuous cycles of denaturation, annealing, and extension, leading to exponential multiple amplification of the target DNA or RNA fragments. PCR, as the basic technology of molecular biology research, has promoted the development of life sciences. However, the general PCR method is complicated and time-consuming, which limits the further development of the technology and is not conducive to quickly obtain a large amount of samples of hepatitis B virus nucleic acid.

SUMMARY

Accordingly, it is necessary to provide a method for rapid amplification of hepatitis B virus nucleic acid that is simple to operate and takes a short time.

A method for rapid amplification of hepatitis B virus nucleic acid comprises:
  mixing a sample containing hepatitis B virus with a nucleic acid release agent followed by adding a PCR premix to obtain a reaction solution, the nucleic acid release agent comprising surfactin, potassium chloride, sodium lauryl sulfonate, and ethanol, the PCR premix comprising deoxy-ribonucleoside triphosphate, a forward primer having a sequence as set forth in SEQ ID NO: 1, a reverse primer having a sequence as set forth in SEQ ID NO: 2, a DNA polymerase, and an amplification buffer;
  placing the reaction solution into a PCR reaction tube to make the reaction solution presented as a thin film with a thickness of less than or equal to 0.1 mm; and
  placing the PCR reaction tube in a PCR amplifier for PCR amplification under a reaction condition set as follows: initial denaturation at 90-100° C. for 10-600 sec, denaturation at 90-100° C. for 0-1 sec, and annealing and extension at 50-65° C. for 0-1 sec.

The method for rapid amplification of hepatitis B virus nucleic acid has been optimized from two aspects. In one aspect, regarding to extraction of the nucleic acid, using strong protein denaturants such as surfactin, potassium chloride, and sodium lauryl sulfonate, the virus shell is quickly destroyed, and the viral nucleic acid is completely released, which is conducive to the rapid PCR amplification. Additionally, it only requires adding the sample, the nucleic acid release agent and other components necessary for PCR to the reaction tube and mixing well, without the need for separate heating and extracting steps such as centrifugation and removal of the supernatant. Moreover, the forward and reverse primers that are used have excellent amplification efficiency, high sensitivity and strong specificity, and are capable of detecting eight genotypes of HBV, which further lays the foundation for rapid PCR amplification. In the other aspect, by placing the reaction solution in the PCR reaction tube to make the reaction solution presented as a thin film with a thickness of less than or equal to 0.1 mm, the heat transfer efficiency can be significantly enhanced, thus the variation difference of temperatures of various parts of the reaction solution is reduced, and the overall temperature consistency and temperature change speed of the reaction solution is increased. This provides another key element for rapid PCR amplification. Combining the above two aspects, in the present disclosure, PCR amplification is performed using the extremely short-time reaction condition as follows: initial denaturation at 90-100° C. for 10-600 sec, denaturation at 90-100° C. for 0-1 sec, and annealing and extension at 50-65° C. for 0-1 sec. In this way, under the premise of ensuring the accuracy and effectiveness of amplification, the time required for each cycle is significantly shortened, and with the increase in the number of cycles, the time and energy savings are becoming more and more obvious. Thus, it achieves the purpose of rapid and simple amplification of hepatitis B virus nucleic acid, thereby providing enough nucleic acid samples for various scientific research.

In one of the embodiments, the reaction condition for PCR amplification are set as follows: initial denaturation at 93-95° C. for 60 sec, denaturation at 93-95° C. for 0 sec, and annealing and extension at 56-58° C. for 0 sec.

In one of the embodiments, the PCR reaction tube has a receiving chamber that is a flat receiving chamber with a thickness less than or equal to 0.1 mm.

In one of the embodiments, the PCR premix further comprises a first probe having a sequence as set forth in SEQ ID NO: 3.

In one of the embodiments, the method further comprises performing fluorescence collection in a temperature rising process between the annealing and extension and the denaturation.

In one of the embodiments, the PCR premix further comprises a ROX reference dye.

In one of the embodiments, the first probe has a carboxyl end modified with a FAM fluorescent group and a hydroxyl end modified with a BHQ1 quencher group.

In one of the embodiments, the PCR premix further comprises an internal standard formed by inserting a DNA having a sequence as set forth in SEQ ID NO: 4 into a pUC18T vector, and a second probe having a sequence as set forth in SEQ ID NO: 5.

In one of the embodiments, the second probe has a carboxyl end modified with a HEX fluorescent group and a hydroxyl end modified with a DABCYL quencher group.

In one of the embodiments, in the nucleic acid release agent, surfactin has a concentration of 0.01-0.5 mmol/L, potassium chloride has a concentration of 50-200 mmol/L, sodium lauryl sulfonate has a concentration of 0.01-2 g/100 mL, and ethanol has a concentration of 0.05-1 mL/100 mL.

DESCRIPTION OF THE EMBODIMENTS

In order to facilitate the understanding of the present disclosure, it will be described more comprehensively below, and preferred embodiments of the present disclosure will be given. However, the present disclosure can be implemented in many different forms and is not limited to the embodiments described herein. On the contrary, these embodiments are provided for the purpose of making the understanding of the present disclosure more thorough and comprehensive.

Unless otherwise defined, all technical and scientific terms used herein have the same meaning as commonly understood by those skilled in the technical field of the present disclosure. The terms used in the specification of the present disclosure are only for the purpose of describing specific embodiments and are not intended to limit the present disclosure. As used herein, the term "and/or" includes any and all combinations of one or more related listed items.

In the embodiments of the present disclosure, a method for rapid amplification of hepatitis B virus nucleic acid comprises the following steps:

S1. mixing a sample containing hepatitis B virus with a nucleic acid release agent followed by adding a PCR premix to obtain a reaction solution, the nucleic acid release agent comprising surfactin, potassium chloride, sodium lauryl sulfonate, and ethanol, the PCR premix comprising deoxy-ribonucleoside triphosphate, a forward primer having a sequence as set forth in SEQ ID NO: 1, a reverse primer having a sequence as set forth in SEQ ID NO: 2, a DNA polymerase, and an amplification buffer;

S2. placing the reaction solution into a PCR reaction tube to make the reaction solution presented as a thin film with a thickness of less than or equal to 0.1 mm; and S3. placing the PCR reaction tube in a PCR amplifier for PCR amplification under a reaction condition set as follows: initial denaturation at 90-100° C. for 10-600 sec, denaturation at 90-100° C. for 0-1 sec, and annealing and extension at 50-65° C. for 0-1 sec. S3. The PCR reaction tube was placed in a PCR amplifier for PCR amplification under a reaction condition set as follows: initial denaturation at 90-100° C. for 10-600 sec, denaturation at 90-100° C. for 0-1 sec, and annealing and extension at 50-65° C. for 0-1 sec.

Figure 1:
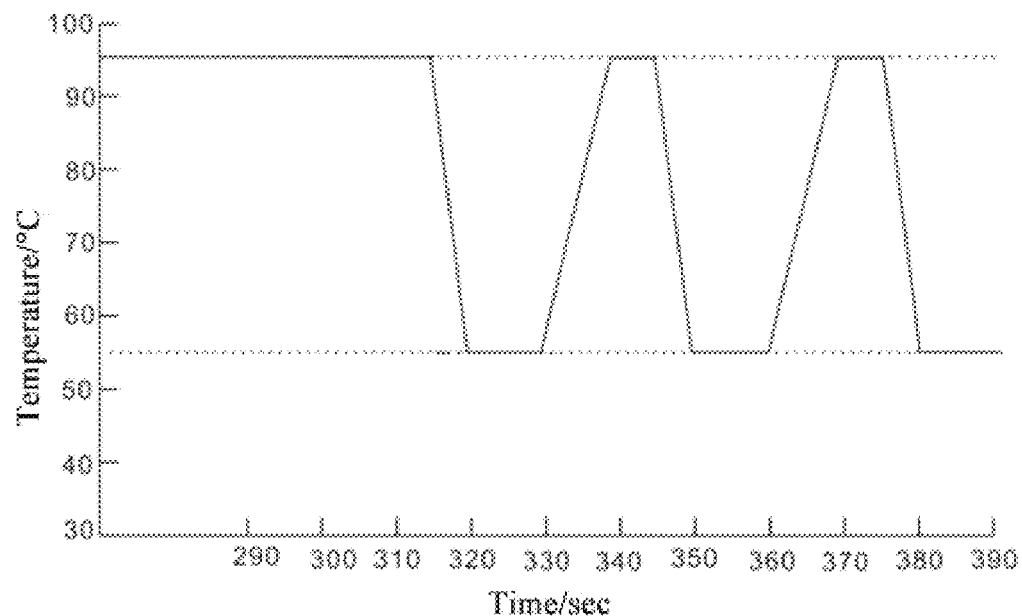
FIG. 1 is a schematic diagram of reaction condition for a traditional PCR.

As shown in FIG. 1, the traditional PCR is performed under a reaction condition as follows: initial denaturation at 94° C. for about 5 min, followed by a certain number of amplification cycles of denaturation at 94° C. for 30 sec (or longer) and annealing and extension at 57° C. for 45 sec (or longer). Therefore, each cycle has a time period for waiting during the period of denaturation and the period of annealing and extension. It takes only a few tens of seconds of waiting from the point of view of a cycle alone, however, the time required increases cumulatively, as the number of cycles increases due to the requirement of continuous cycles for achieving the amplification of the target DNA or RNA, resulting in a lot of time consumption eventually.

The method for rapid amplification of hepatitis B virus nucleic acid has been optimized from two aspects. In one aspect, regarding to extraction of the nucleic acid, using strong protein denaturants such as surfactin, potassium chloride, and sodium lauryl sulfonate, the virus shell is quickly destroyed, and the viral nucleic acid is completely released, which is conducive to the rapid PCR amplification. Additionally, it only requires adding the sample, the nucleic acid release agent and other components necessary for PCR to the reaction tube and mixing well, without the need for separate heating and extracting steps such as centrifugation and removal of the supernatant. Moreover, the forward and reverse primers that are used have excellent amplification efficiency, high sensitivity and strong specificity, and are capable of detecting eight genotypes of HBV, which further lays the foundation for rapid PCR amplification. In the other aspect, by placing the reaction solution in the PCR reaction tube to make the reaction solution presented as a thin film with a thickness of less than or equal to 0.1 mm, the heat transfer efficiency can be significantly enhanced, thus the variation difference of temperatures of various parts of the reaction solution is reduced, and the overall temperature consistency and temperature change speed of the reaction solution is increased. This provides another key element for rapid PCR amplification. Combining the above two aspects, in the present disclosure, PCR amplification is performed using the extremely short-time reaction condition as follows: initial denaturation at 90-100° C. for 10-600 sec, denaturation at 90-100° C. for 0-1 sec, and annealing and extension at 50-65° C. for 0-1 sec. In this way, under the premise of ensuring the accuracy and effectiveness of amplification, the time required for each cycle is significantly shortened, and with the increase in the number of cycles, the time and energy savings are becoming more and more obvious. Thus, it achieves the purpose of rapid and simple amplification of hepatitis B virus nucleic acid, thereby providing enough nucleic acid samples for various scientific research.

Figure 2:
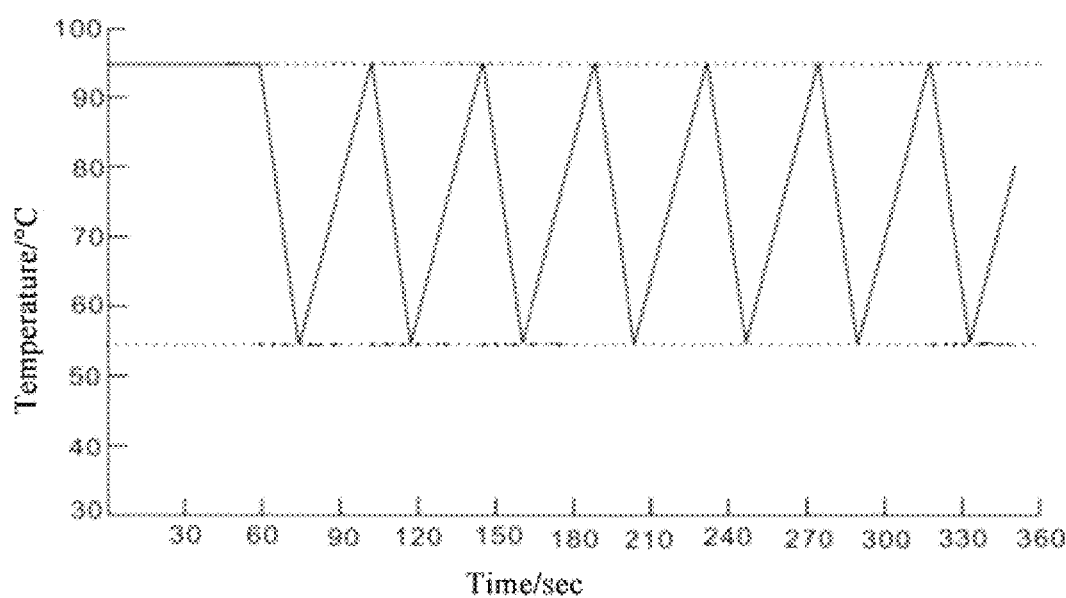
FIG. 2 is a schematic diagram of reaction condition for PCR in an embodiment.

Preferably, the reaction condition for PCR amplification is set as follows: initial denaturation at 93-95° C. for 60 sec, denaturation at 93-95° C. for 0 sec, and annealing and extension at 56-58° C. for 0 sec. The time of denaturation and of annealing and extension refers to the condition of a parameter set on the PCR amplifier. The time set as 0 sec means that the temperature always changes without a maintenance stage, as shown in FIG. 2. In this way, after the earliest initial denaturation in which the temperature of PCR remains constant, the temperature is always in a state of change. Therefore, the whole process has low requirements on the precision of temperature control and the corresponding measures to implement temperature control (such as slowing down the temperature increasing and decreasing speed in advance), which reduces the technical difficulty of temperature control and saves the manufacturing cost of the PCR instrument.

Figure 3:
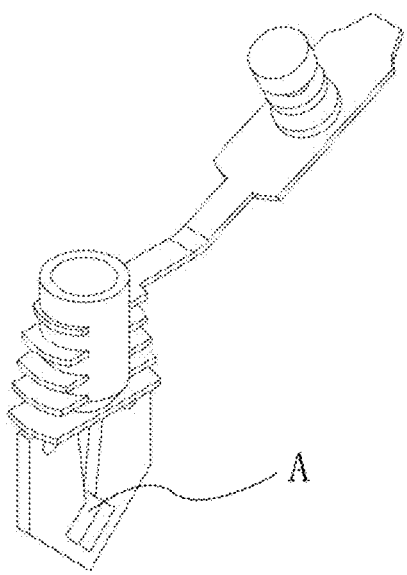
FIG. 3 is a schematic structural diagram of a PCR reaction tube in an embodiment.
Figure 4:
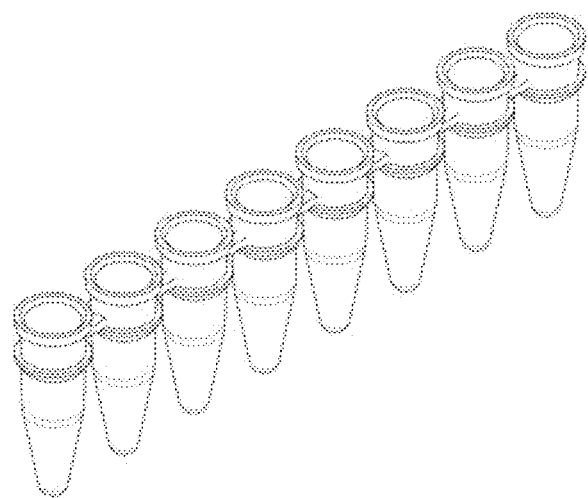
FIG. 4 is a schematic structural diagram of a traditional PCR reaction tube.

In an embodiment, the PCR reaction tube has a receiving chamber that is a flat receiving chamber with a thickness less than or equal to 0.1 mm, for example, a receiving chamber A of the PCR reaction tube in FIG. 3. Currently, all the PCR reaction containers commonly used are cone-shaped blind-hole containers as shown in FIG. 4, with an inverted cone structure at the bottom. This structure is conducive to the increase of the temperature change rate of the bottommost part, but it is not obviously conducive to the increase of the temperature change rate of the entire reaction liquid and is difficult to ensure the consistency of the temperature of the reaction liquid at the edge with that in the center during the temperature change. In order to ensure the effectiveness and accuracy of the amplification, it is necessary to wait for the central location to reach the specified temperature before continuing to change the temperature, which reduces the speed of PCR amplification and wastes a great deal of energy and time. In this embodiment, the flat design of the PCR reaction tube facilitates making the cross-sectional thickness of the liquid phase substance in the container much smaller than that in the traditional conical tube container. Thus, the direct contact area of the reaction container with the liquid phase substance in the reaction container is greatly increased, and the liquid phase substance forms a thin film with a thickness of less than or equal to 0.1 mm, which significantly improves the heat transfer efficiency and helps speed up the PCR amplification. It can be understood that the specific structure of the PCR reaction tube is not limited to the structure as shown in FIG. 3, as long as the reaction liquid can be made presented as a thin film with a thickness of less than or equal to 0.1 mm.

In an embodiment, the PCR premix further comprises a first probe having a sequence as set forth in SEQ ID NO: 3. During PCR amplification, a specific fluorescent probe is added while adding a pair of primers. The probe is an oligonucleotide, with two ends labeled with one fluorescence reporter group and one fluorescence quencher group, respectively. For a complete probe, the fluorescent signal emitted by the reporter group is absorbed by the quencher group, while during PCR amplification, the Taq enzyme cleaves and degrades the probe with its exonuclease activity to separate the fluorescence reporter group from the fluorescence quencher group, so that the fluorescent signal can be received by a fluorescence monitoring system. In other words, every time one DNA strand is amplified, one fluorescent molecule is formed. This realizes complete synchronization of the accumulation of fluorescent signals with the formation of PCR products, which is conducive to nucleic acid quantification through the fluorescence monitoring system. Preferably, the first probe has a carboxyl end modified with a FAM fluorescent group and a hydroxyl end modified with a BHQ1 quencher group. It can be understood that the carboxyl end can be modified with a fluorescent group selected from TET, JOE, HEX, and the like, and that the hydroxy end can be modified with a quencher group selected from TAMRA, BHQ2, BHQ3, and the like. The fluorescent group and the quencher group are not limited thereto.

In an embodiment, the method for rapid amplification of hepatitis B virus nucleic acid further comprises performing fluorescence collection in a temperature changing process between the annealing and extension and the denaturation. The fluorescence collection is performed, if fluorescence quantification is required, in the temperature changing process, thanks to the setting of parameters of the above reaction condition of PCR. Thus, there is no need to maintain a constant temperature for a long time, which can reduce the waste of energy and time.

In an embodiment, the PCR premix further comprises a ROX reference dye. If fluorescence quantification is required, normalization correction can be performed by adding the ROX reference dye since errors caused by various factors are difficult to avoid, thereby greatly improving the stability and repeatability of the test results.

In an embodiment, the PCR premix further comprises an internal standard formed by inserting a DNA having a sequence as set forth in SEQ ID NO: 4 into a pUC18T vector, and a second probe having a sequence as set forth in SEQ ID NO: 5 The second probe has a carboxyl end modified with a HEX fluorescent group and a hydroxyl end modified with a DABCYL quencher group. In this way, by adding the internal standard, it can be quickly identified for the cause when amplification is failed due to PCR interfering substances in the sample. It can be understood that the second probe has the carboxyl end that can be labeled with a fluorescent group different from that of the first probe, such as TET, JOE, FAM, and the like, and the hydroxyl end that can be labeled with a quencher group such as BHQ1, TAMRA, BHQ2, BHQ3, and the like. The fluorescent group and the quencher group are not limited thereto.

In an embodiment, in the nucleic acid release agent, surfactin has a concentration of 0.01-0.5 mmol/L, potassium chloride has a concentration of 50-200 mmol/L, sodium lauryl sulfonate has a concentration of 0.01-2 g/100 mL, and ethanol has a concentration of 0.05-1 mL/100 mL.

Specific examples are described as follows. It should be noted that, in order to show whether the PCR amplification is accurate and effective, the first probe and the ROX reference dye were added in all the following examples and the fluorescence collection was performed correspondingly. However, in the practical amplification of hepatitis B virus nucleic acid, whether or not to add the first probe and the ROX reference dye can be chosen as needed. In fluorescent quantitative PCR, Ct value means the number of cycles experienced for the fluorescent signal to reach a set threshold in each reaction tube. Studies have shown that the Ct value of each sample has a linear relationship with the logarithm of the initial copy number of the sample. The more the initial copy number, the smaller the Ct value. Using a standard with a known initial copy number, a standard curve, in which the abscissa represents the logarithm of the initial copy number and the ordinate represents the Ct value, can be obtained. Therefore, once the Ct value of the sample is obtained, the initial copy number of the sample and its logarithm (LOG value) can be calculated according to the standard curve.

The operating steps were as follows:

A stock solution, containing an amplification buffer, 0.2 mmol/L of deoxy-ribonucleoside triphosphate, 40 mmol/L-200 mmol/L of a ROX reference dye, 0.2 μmol/L-0.4 μmon of a forward primer and a reverse primer, and 0.2 μmol/L-0.4 μmon of a first probe, was provided. An enzyme solution containing Taq enzyme at a concentration of 1 U/μL was provided. A nucleic acid release agent, containing 0.01 mmol/L of surfactin, 50 mmol/L of potassium chloride, 0.01 g/100 mL of sodium lauryl sulfonate, and 0.05 mL/100 mL of ethanol, was provided.

38~44 μL of the stock solution was mixed well with 1-2 mL of the enzyme solution to obtain a PCR premix, which was centrifuged shortly for later use. With the container as shown in FIG. 3 used as a PCR reaction tube, 2-5 μL of the nucleic acid release agent and 3-5 μL of a sample were added to each of the PCR reaction tubes, followed by pipetting up and down 3-5 times for well mixing. Then 40-45 μL of the PCR premix was added to each of the PCR reaction tubes, and pipetting up and down 2-3 times for well mixing. After capping the tubes, the tubes were centrifuged at 2000 rpm for 30 sec. The PCR reaction tubes were placed in the fluorescence quantitative PCR amplifier for PCR amplification according to the set reaction condition. After completion of the reaction, the instrument saved the results automatically and data such as Ct values, LOG values, and amplification curves was acquired.

Examples 1 to 16

Figure 5:
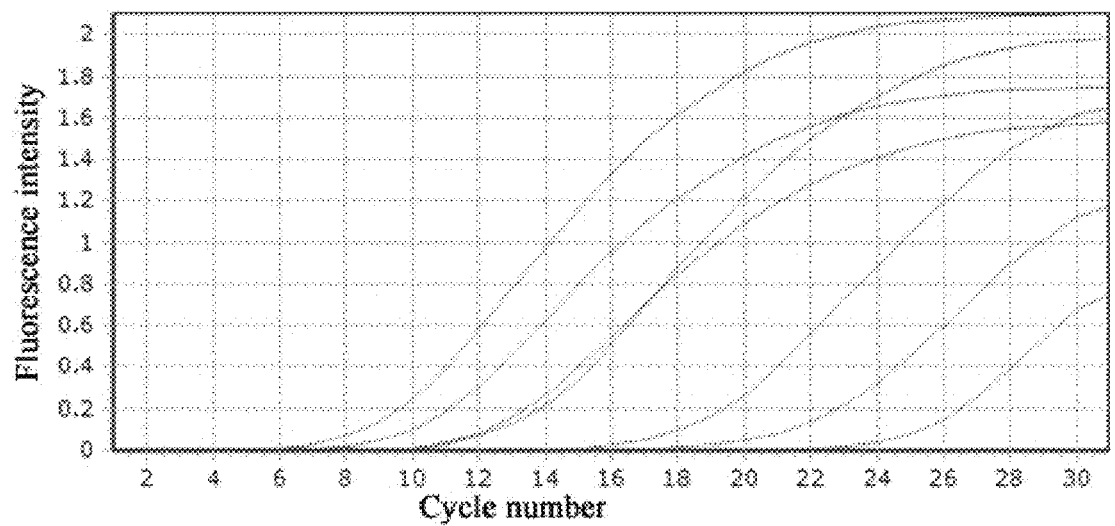
FIG. 5 is a graph of amplification curves of Examples 1 to 16.

According to the operating steps, 16 samples containing hepatitis B virus were amplified by PCR under a reaction condition as follows: initial denaturation at 94° C. for 1 min, followed by 40 cycles of denaturation at 94° C. for 0 sec and annealing and extension at 57° C. for 0 sec. Fluorescence collection was performed in the temperature rising process from 57° C. to 94° C. in each cycle. The total time of the amplification program was 15 min. The PCR instrument used is a GNM-C7-8 real-time fluorescent quantitative PCR instrument produced by Genome Biotechnology Co., Ltd. The amplification curves were shown in FIG. 5. It can be seen that Examples 1 to 16 had amplification curves maintaining a good shape and had higher amplification efficiency. The logarithmic values (LOG values) were shown in Table 1.

In addition, for a blank sample (a sample without hepatitis B virus) that was amplified according to a method as same as that in Examples 1 to 16, no false-positive results were found.

Comparative Examples 1 to 16

Figure 6:
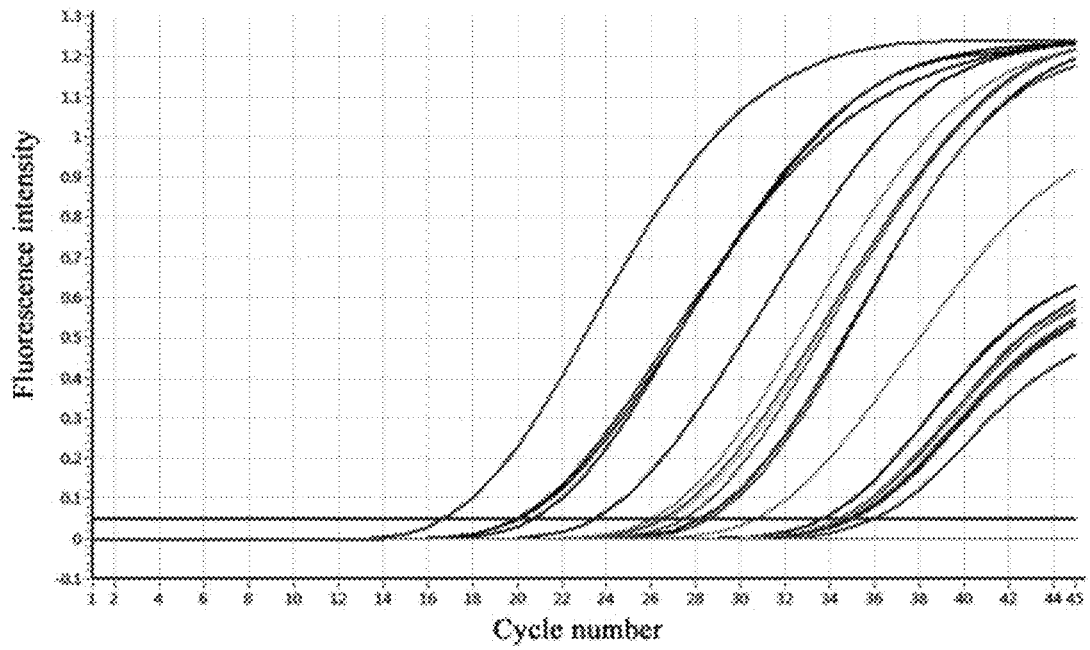
FIG. 6 is a graph of amplification curves of Comparative Examples 1 to 16.

According to the operating steps, the same 16 samples containing hepatitis B virus were amplified by PCR under a reaction condition as follows: initial denaturation at 94° C. for 5 min, followed by 45 cycles of denaturation at 94° C. for 15 sec and annealing and extension at 57° C. for 30 sec, accompanied by fluorescence collection. The total time of the amplification program was 72 min. The PCR instrument used is a GNM-C7-8 real-time fluorescent quantitative PCR instrument produced by Genome Biotechnology Co., Ltd. The amplification curves were shown in FIG. 6. The sample concentrations and LOG values were shown in Table 1.

TABLE 1

| Sample No. | Comparative Examples 1 to 16 Concentration | LOG value | Examples 1 to 16 Ct value | LOG value | LOG difference |
|---|---|---|---|---|---|
| 1 | 1.84E+03 | 3.26 | 24.11 | 3.28 | 0.02 |
| 2 | 1.26E+03 | 3.10 | 23.80 | 3.37 | 0.27 |
| 3 | 2.32E+05 | 5.37 | 17.43 | 5.39 | 0.02 |
| 4 | 6.20E+05 | 5.79 | 15.32 | 5.93 | 0.14 |
| 5 | 1.88E+03 | 3.27 | 22.05 | 3.90 | 0.63 |
| 6 | 3.94E+08 | 8.60 | 6.92 | 8.46 | −0.14 |
| 7 | 6.54E+02 | 2.82 | 26.11 | 2.68 | −0.14 |
| 8 | 1.41E+03 | 3.15 | 24.47 | 3.17 | 0.02 |
| 9 | 1.26E+03 | 3.10 | 25.52 | 2.86 | −0.24 |
| 10 | 1.87E+03 | 3.27 | 24.18 | 3.26 | −0.01 |
| 11 | 1.39E+05 | 5.14 | 18.11 | 5.09 | −0.06 |
| 12 | 3.11E+03 | 3.49 | 24.12 | 3.28 | −0.22 |
| 13 | 1.52E+03 | 3.18 | 24.35 | 3.21 | 0.03 |
| 14 | 1.09E+05 | 5.04 | 20.01 | 4.52 | −0.52 |
| 15 | 2.53E+07 | 7.40 | 11.33 | 7.13 | −0.27 |
| 16 | 4.36E+07 | 7.64 | 9.08 | 7.81 | 0.17 |

Figure 7:
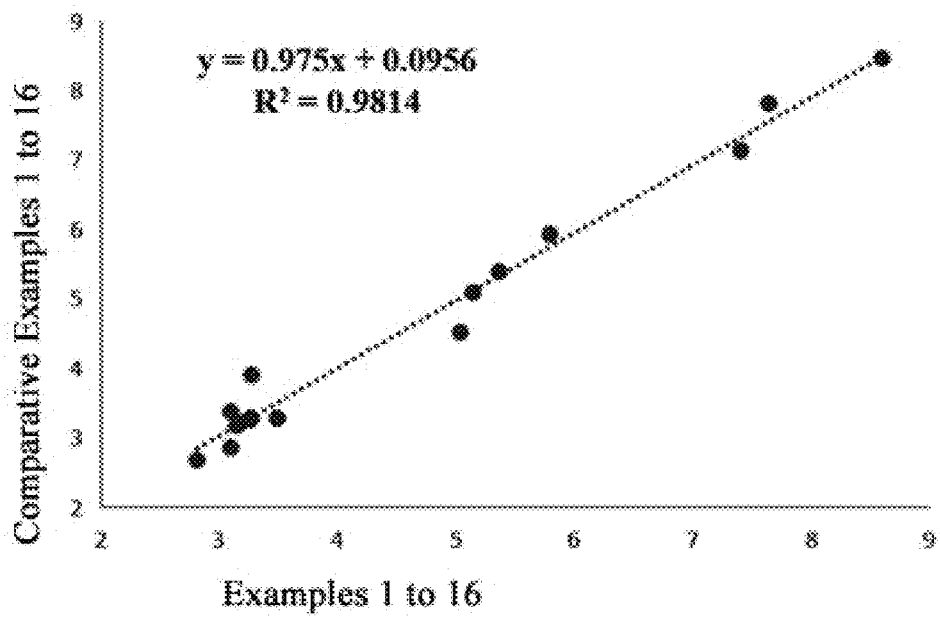
FIG. 7 is a correlation analysis diagram for Examples 1 to 16 and Comparative Examples 1 to 16.

According to Table 1, there was little difference between the LOG values of Examples 1 to 16 and those of Comparative Examples 1 to 16 which used reaction condition for traditional PCR, suggesting that nucleic acid amplification of Examples 1 to 16 had the same effectiveness and accuracy as those of Comparative Examples 1 to 16, however, spent significantly reduced time, with the Ct value of each sample maintaining a good correlation with the logarithm of the initial concentration of the sample. Correlation analysis was performed on the LOG values of Examples 1 to 16 and the LOG values of Comparative Examples 1 to 16. The results were shown in FIG. 7, also proving a good correlation.

Comparative Examples 17 to 32

According to the operating steps, the same 16 samples containing hepatitis B virus were amplified differently from Examples 1 to 16. The differences were as follows:

For reagents preparation, a DNA extraction solution and an HBV-PCR reaction solution were provided for use. The components of the DNA extraction solution were chelex100, Tris-HCL, NaOH, Triton-100, NP-40, and EDTA. The components of the HBV-PCR reaction solution were primers, a probe, dN(U)TP, buffer, DNA polymerase, and UNG enzyme. The primers have sequences which are different from SEQ ID NO: 1 and SEQ ID NO: 2. The HBV-PCR reaction solution was added to a centrifuge tube followed by well mixing by shaking. After a short centrifugation, the solution was divided into 45-uL aliquot per PCR reaction tube.

For DNA extraction, to 100 uL of a sample, the same amount of DNA concentration solution (PEG6000, NaCl) was added, followed by well mixing by shaking for 5 sec. After centrifugation at 10,000 rpm for 10 min, the supernatant was removed, leaving the pellets, to which 30 uL of DNA was added followed by well mixing by vigorous shaking for 10 sec. After a short centrifugation, the resultant was thermostatically treated at 100° C. for 10 min and centrifuged at 10,000 rpm for 5 min for use. For PCR amplification, 5 uL of the treated supernatant of the sample was added to each tube containing the prepared PCR reaction solution, and centrifuged shortly for later use. The PCR reaction tubes were placed in the fluorescence quantitative PCR amplifier for PCR amplification according to the reaction condition for PCR in Examples 1 to 16. The amplification curves were shown in FIG. 8. The LOG values were shown in Table 2.

TABLE 2

| Sample No. | Comparative Examples 1 to 16 | | Comparative Examples 17 to 32 | | |
|---|---|---|---|---|---|
| | Concentration | LOG value | Ct value | Equivalent LOG value | LOG difference |
| 1 | 1.84E+03 | 3.26 | — | — | — |
| 2 | 1.26E+03 | 3.10 | — | — | — |
| 3 | 2.32E+05 | 5.37 | 27.43 | 2.28 | −3.09 |
| 4 | 6.20E+05 | 5.79 | 26.49 | 2.56 | −3.23 |
| 5 | 1.88E+03 | 3.27 | — | — | — |
| 6 | 3.94E+08 | 8.60 | 17.73 | 5.20 | −3.39 |
| 7 | 6.54E+02 | 2.82 | — | — | — |
| 8 | 1.41E+03 | 3.15 | — | — | — |
| 9 | 1.26E+03 | 3.10 | — | — | — |
| 10 | 1.87E+03 | 3.27 | — | — | — |
| 11 | 1.39E+05 | 5.14 | — | — | — |
| 12 | 3.11E+03 | 3.49 | — | — | — |
| 13 | 1.52E+03 | 3.18 | — | — | — |
| 14 | 1.09E+05 | 5.04 | 28.43 | 1.98 | −3.06 |
| 15 | 2.53E+07 | 7.40 | 25.12 | 2.98 | −4.43 |
| 16 | 4.36E+07 | 7.64 | 20.43 | 4.39 | −3.25 |

Figure 8:
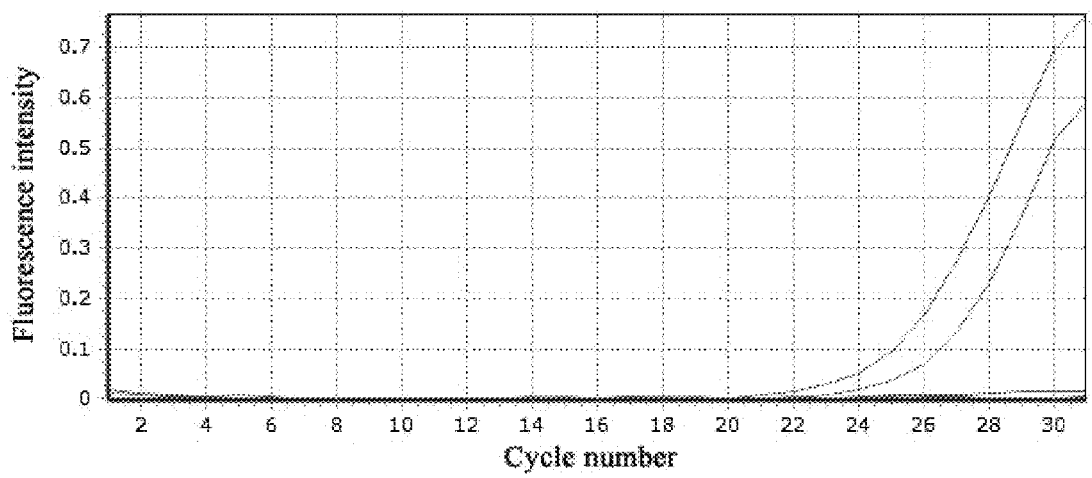
FIG. 8 is a graph of amplification curves of Comparative Examples 17 to 32.

According to FIG. 8 and Table 2, it is not possible to present the amplification curves, thus to obtain the Ct values in most of the Comparative Examples 17 to 32. For the few Comparative Examples that can get Ct values, their LOG values were far from those of Comparative Examples 1 to 16 which used reaction condition for traditional PCR, suggesting that nucleic acid amplification of Comparative Examples 17 to 32 had very poor effectiveness and accuracy and thus was failed, with the Ct value of each sample maintaining no good correlation with the logarithm of the initial concentration of the sample.

Comparative Examples 33 to 48

According to the operating steps, the same 16 samples containing hepatitis B virus were amplified differently from Examples 1 to 16. The difference lies on that the cone-shaped blind-hole container as shown in FIG. 4 was used as the PCR reaction tube. The amplification curves were shown in FIG. 9. The LOG values were shown in Table 3.

TABLE 3

| Sample No. | Comparative Examples 1 to 16 | | Comparative Examples 33 to 48 | | |
|---|---|---|---|---|---|
| | Concentration | LOG value | Ct value | Equivalent LOG value | LOG difference |
| 1 | 1.84E+03 | 3.26 | — | — | — |
| 2 | 1.26E+03 | 3.10 | — | — | — |
| 3 | 2.32E+05 | 5.37 | — | — | — |
| 4 | 6.20E+05 | 5.79 | — | — | — |
| 5 | 1.88E+03 | 3.27 | — | — | — |
| 6 | 3.94E+08 | 8.60 | — | — | — |
| 7 | 6.54E+02 | 2.82 | — | — | — |
| 8 | 1.41E+03 | 3.15 | — | — | — |
| 9 | 1.26E+03 | 3.10 | — | — | — |
| 10 | 1.87E+03 | 3.27 | — | — | — |
| 11 | 1.39E+05 | 5.14 | — | — | — |
| 12 | 3.11E+03 | 3.49 | — | — | — |
| 13 | 1.52E+03 | 3.18 | — | — | — |
| 14 | 1.09E+05 | 5.04 | — | — | — |
| 15 | 2.53E+07 | 7.40 | — | — | — |
| 16 | 4.36E+07 | 7.64 | — | — | — |

Figure 9:
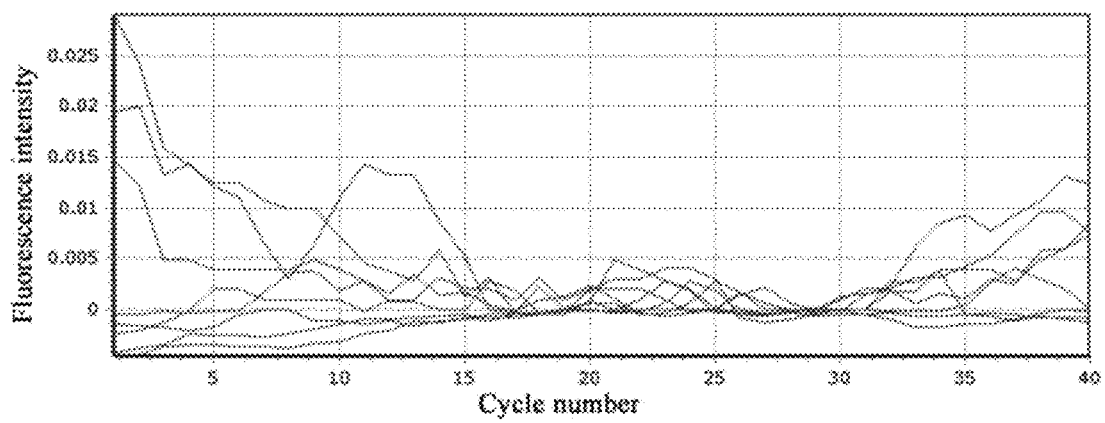
FIG. 9 is a graph of amplification curves of Comparative Examples 33-48.

According to FIG. 9 and Table 3, it is not possible to present the amplification curves, thus to obtain the Ct values in all of the Comparative Examples 33 to 48, suggesting that nucleic acid amplification of Comparative Examples 33 to 48 had very poor effectiveness and accuracy and thus was failed, with the Ct value of each sample maintaining no good correlation with the logarithm of the initial concentration of the sample.

The technical features of the above-mentioned embodiments can be combined arbitrarily. In order to make the description concise, all possible combinations of the various technical features in the foregoing embodiments are not described. However, the combination of these technical features should be considered within the scope of this specification, as long as there is no contradiction.

The above-mentioned embodiments only present several embodiments of the present disclosure, whose descriptions are more specific and detailed but should not be thus understood as limiting the scope of the present disclosure. It should be indicated that for those of ordinary skill in the art, several modifications and improvements can be made without departing from the concept of the present disclosure, and these all fall within the protection scope of the present disclosure. Therefore, the protection scope of the present disclosure should be subject to the appended claims.

What is claimed is:

1. A method for rapid amplification of hepatitis B virus nucleic acid, comprising:
    mixing a sample containing hepatitis B virus with a nucleic acid release agent followed by adding a PCR premix to obtain a reaction solution, the nucleic acid release agent comprising surfactin having a concentration of 0.01-0.5 mmol/L, potassium chloride having a concentration of 50-200 mmol/L, sodium lauryl sulfonate having a concentration of 0.01-2 g/100 mL, and ethanol having a concentration of 0.05-1 mL/100 mL, the PCR premix comprising deoxy-ribonucleoside triphosphate, a forward primer having the sequence as set forth in SEQ ID NO: 1 and a concentration of 0.2 µmol/L-0.4 µmol/L, a reverse primer having the sequence as set forth in SEQ ID NO: 2 and a concentration of 0.2 µmol/L-0.4 µmol/L, a DNA polymerase, and an amplification buffer;
    placing the reaction solution into a PCR reaction tube having a flat receiving chamber with a thickness less than or equal to 0.1 mm to make the reaction solution presented as a thin film with a thickness of less than or equal to 0.1 mm; and
    placing the PCR reaction tube in a PCR amplifier for PCR amplification under a reaction condition set as follows: initial denaturation at 93-95° C. for 60 sec, denaturation at 93-95° C. for 0 sec, and annealing and extension at 56-58° C. for 0 sec.

2. The method according to claim 1, wherein the PCR premix further comprises a first fluorescent probe having the sequence as set forth in SEQ ID NO: 3.

3. The method according to claim 2, further comprising performing fluorescence collection in a temperature rising process from 50-65° C. to 90-100° C. in the extension step in each cycle.

4. The method according to claim 2, wherein the PCR premix further comprises a ROX reference dye.

5. The method according to claim 2, wherein the first probe has a carboxyl end modified with a FAM fluorescent group and a hydroxyl end modified with a BHQ1 quencher group.

6. The method according to claim 2, wherein the PCR premix further comprises an internal standard formed by inserting a DNA having the sequence as set forth in SEQ ID NO: 4 into a pUC18T vector, and a second probe having the sequence as set forth in SEQ ID NO:5.

7. The method according to claim 6, wherein the second probe has a carboxyl end modified with a HEX fluorescent group and a hydroxyl end modified with a DABCYL quencher group.

* * * * *

SEQUENCE LISTING

```
<160> NUMBER OF SEQ ID NOS: 5

<210> SEQ ID NO 1
<211> LENGTH: 26
<212> TYPE: DNA
<213> ORGANISM: Hepatitis B virus

<400> SEQUENCE: 1
atcgctggat gtgtctgctg cgtttt                                    26

<210> SEQ ID NO 2
<211> LENGTH: 28
<212> TYPE: DNA
<213> ORGANISM: Hepatitis B virus

<400> SEQUENCE: 2
ctggaattag aggacaaacg ggcaacat                                  28
```

```
<210> SEQ ID NO 3
<211> LENGTH: 38
<212> TYPE: DNA
<213> ORGANISM: Hepatitis B virus

<400> SEQUENCE: 3
cctcttcatc ctgctgctat gcctcatctt cttattgg                              38

<210> SEQ ID NO 4
<211> LENGTH: 97
<212> TYPE: DNA
<213> ORGANISM: Artificial Sequence
<220> FEATURE:
<223> OTHER INFORMATION: internal standard

<400> SEQUENCE: 4
atcgctggat gtgtctgcgg cgttttatat cttcctccat cctgctaggt gcctcatctt      60
cttagctcta tgttgcccgt ttgtcctcta attccag                               97

<210> SEQ ID NO 5
<211> LENGTH: 36
<212> TYPE: DNA
<213> ORGANISM: Artificial Sequence
<220> FEATURE:
<223> OTHER INFORMATION: probe

<400> SEQUENCE: 5
ttcctccatc ctgctaggtg cctcatcttc ttagct                                36
```